United States Patent [19]

Merz et al.

[11] 3,982,005
[45] Sept. 21, 1976

[54] 2-TETRAHYDROFURFURYL-5-(METHYL OR PHENYL)-9β-METHYL-2'-OXY-6,7-BENZOMORPHANS AND SALTS THEREOF

[75] Inventors: Herbert Merz; Adolf Langbein, both of Ingelheim am Rhein; Gerhard Walther; Klaus Stockhaus, both of Bingen (Rhine), all of Germany

[73] Assignee: Boehringer Ingelheim GmbH, Ingelheim am Rhein, Germany

[22] Filed: July 30, 1975

[21] Appl. No.: 600,374

[30] Foreign Application Priority Data

Aug. 5, 1974 Germany............................ 2437610

[52] U.S. Cl........................... 424/267; 260/293.54; 260/DIG. 13
[51] Int. Cl.²...................................... C07D 221/26
[58] Field of Search............... 260/293.54, DIG. 13; 424/267

[56] References Cited
UNITED STATES PATENTS

| | | |
|---|---|---|
| 2,924,603 | 2/1960 | Gordon et al................... 260/293.4 |
| 3,700,734 | 10/1972 | Robinson et al............... 260/293.54 |
| 3,823,150 | 7/1974 | Merz et al...................... 260/293.54 |
| 3,917,606 | 11/1975 | Merz et al.......................... 260/285 |

*Primary Examiner*—G. Thomas Todd
*Attorney, Agent, or Firm*—Hammond & Littell

[57] ABSTRACT

Compounds of the formula

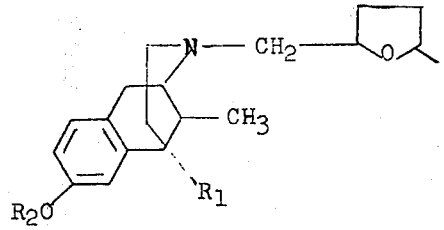

wherein $R_1$ is methyl or phenyl, and
$R_2$ is hydrogen, methyl or acetyl, and non-toxic, pharmacologically acceptable acid addition salts thereof; the compounds as well as the salts are useful as analgesics.

11 Claims, No Drawings

2-TETRAHYDROFURFURYL-5-(METHYL OR PHENYL)-9β-METHYL-2'-OXY-6,7-BENZOMORPHANS AND SALTS THEREOF

This invention relates to novel 2-tetrahydrofurfuryl-5-(methyl or phenyl)-9β-methyl-2'-oxy-6,7-benzomorphans and non-toxic acid addition salts thereof, as well as to various methods of preparing these compounds.

More particularly, the present invention relates to a novel class of compounds represented by the formula

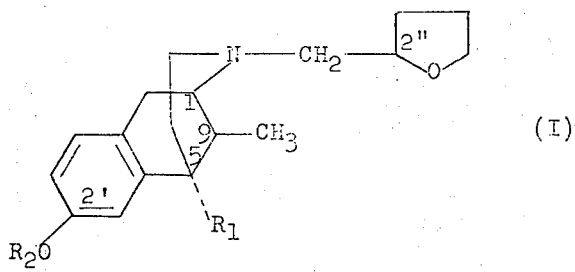

(I)

wherein
$R_1$ is methyl or phenyl, and
$R_2$ is hydrogen, methyl or acetyl, and non-toxic, pharmacologically acceptable acid addition salts thereof.

In formula I above the broken line indicates that the substituents in the 5- and 9-positions of the carbocyclic ring are arranged in trans-configuration.

A preferred sub-genus is constituted by those compounds of the formula I wherein $R_2$ is hydrogen and $R_1$ has the meanings previously defined. Especially preferred is 2-tetrahyrofurfuryl-2'-hydroxy-5,9β-dimethyl-6,7-benzomorphan and its stereoisomers.

In the light of the foregoing definition of the compounds embraced by formula I, the following situation results with respect to stereoisomerism: The norbenzomorphans from which the compounds of the present invention are derived, that is, the compounds of the formula

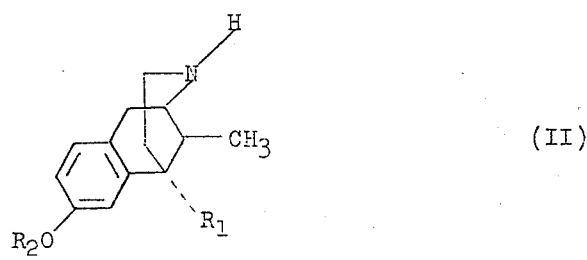

(II)

wherein $R_1$ and $R_2$ have the meanings defined in connection with formula I, comprise three centers of asymmetry.

However, due to the rigid incorporation of the C-1 and C-5 centers of asymmetry into a bridged ring system and because of the fixed position of the C-9 center of asymmetry (limitation to the β-series) the nor-compounds of the formula II exist only in a single racemic form and as the corresponding optical antipodes as follows:

| Designation | Form of II | Configuration |
|---|---|---|
| (±) - II | racemic | — |
| (−) - II | levo-rotatory | 1 R, 5 R, 9 S |
| (+) - II | dextro-rotatory | 1 S, 5 S, 9 R |

The N-tetrahydrofurfuryl-substitution of the nor-compound introduces an additional center of asymmetry into the molecule (at C-2" in the tetrahydrofuran ring). Therefore, it is to be expected that formula I, as above defined, embraces two series (I, 1) and (I, 2) of racemic diastereoisomers and the corresponding optical antipodes, which owe their existence to the following possible combinations:

| Designation | Configuration Benzomorphan moiety | N-tetrahydrofurfuryl group | |
|---|---|---|---|
| I,1 | 1 R, 5 R, 9 S-(−) | D-(−) | racemic diastereoisomer 1 |
| | 1 S, 5 S, 9 R-(+) | L-(+) | |
| I,2 | 1 R, 5 R, 9 S-(−) | L-(+) | racemic diastereoisomer 2 |
| | 1 S, 5 S, 9 R-(+) | D-(−) | |

Which of the optical antipodes belonging to (I,1) or (I,2), respectively, is the levo-rotatory form or the dextro-rotatory form can fundamentally not be determined solely on the basis of configuration, but can be ascertained only by measurement in a polarimeter.

As to the optical rotations which we investigated, we found that the direction of optical rotation of the precursor of the formula II is not altered by the introduction of the D-(−)- or L-(+)-tetrahydrofurfuryl substituent.

As far as the nomenclature of the compounds of the formula I is concerned, the naming of the optically active embodiments offers no difficulties, as can be seen from the above table. Thus, when the designation 1R, 5R, 9S or 1S, 5S, 9R is used, the configuration at C-9 is clearly established, so that the "β" can be omitted in the chemical nomenclature. On the other hand, in connection with the racemic compounds it is not possible to predict which of the two possible diastereoisomers is obtained; hence, in the following description of the present invention both racemic diastereoisomers are designated by (±) and differentiated from each other by the supplement "diastereoisomer 1" or "diastereoisomer 2," where 1 and 2 merely indicates the sequence in which they were isolated.

The compounds embraced by formula I, as above defined, may be prepared by a number of different methods among which the following have proved to be particularly convenient and efficient:

Method A

By alkylating a norbenzomorphan of the formula II above with a tetrahydrofurfuryl compound of the formula

(III)

wherein X is a nucleophylically exchangeable substituent, such as arylsulfonyloxy, aralkylsulfonyloxy, alkylsufonyloxy or preferably halogen, especially chlorine, bromine or iodine.

The calculated quantity of the alkylating agent of the formula III or preferably an excess thereof is provided, and the reaction is advantageously performed in the presence of an acid-binding agent, such as triethylamin,e dicyclohexylethylamine, sodium carbonate, potassium carbonate, calcium oxide or preferably sodiumbicarbonate. Although it is not required to use a solvent, the performance of the reaction in an inert solvent, such as chloroform, toluene, ethanol, nitromethane, tetrahydrofuran, dimethylsulfoxide or preferably dimethylformamide, is more advantageous. Mixtures of two or more of these solvents may also be used. Finally, an excess of the alkylating agent, for example an excess of tetrahydrofurfuryl bromide, may serve as the solvent as well. The reaction temperature is variable in wide limits, the lower limit being given by too slow a reaction rate, and the upper limit being given by an increased occurrence of side-reactions. Temperatures between 50°, and 150°C, preferably 100°C, are acceptable. If the reaction is performed with a less reactive alkylating agent, such as with tetrahydrofurfuryl chloride, the reaction may be accelerated by addition of a catalytic or equimolar quantity of potassium iodide or sodium iodide.

Method B

By reducing a carbonamide or thioamide of the formula

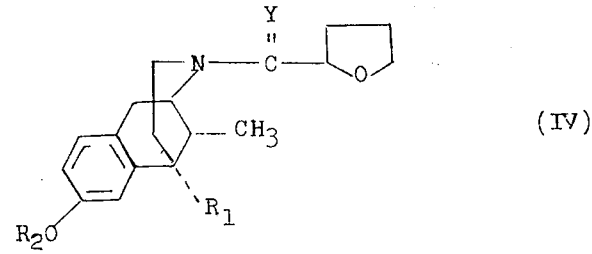

(IV)

wherein $R_1$ and $R_2$ have the same meanings as in formula I and Y is oxygen or sulfur.

The reduction of a carbonamide of the formula IV (Y is oxygen) may be effected pursuant to various methods. Especially suitable is the reduction with a complex hydride of high reducing power, especially with lithium aluminum hydride. The hydride is provided in the calculated amount or in excess, preferably up to twice the calculated amount. The reaction is advantageously carried out in an inert solvent, preferably in diethyl ether, diisopropyl ether or especially tetrahydrofuran. The reaction temperature is variable within wide limits and lies advantageously between 0°C and the boiling point of the solvent.

During the reduction of an O-acetyl derivative of a carbonamide of the formula IV ($R_2$ is acetyl and Y is oxygen) with a complex metal hydride, such as during the reduction with lithium aluminum hydride, not only the carbonyl group is reduced, but simultaneously also the O-acetyl group is reductively split off, and in this case a compound of the formula I is obtained wherein $R_2$ is hydrogen.

The reduction of a thioamide of the formula IV (Y is sulfur) takes place much more easily than that of a carbonamide. It may be effected with a complex hydride or with nascent hydrogen (generated, for example, by zinc/hydrochloric acid, zinc/acetic acid or aluminum amalgam/water); it is also possible to desulfurize the thioamide with Raney nickel, or to effect the reduction electrochemically. By using a reducing agent with stronger reducing power, O-aceyl groups may simultaneously be split off reductively. In this case a compound of the formula I wherein $R_2$ is hydrogen is obtained.

Method C

By reducing a compound of the formula

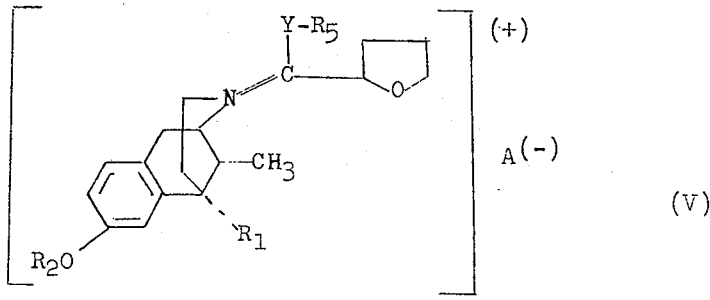

(V)

wherein $R_1$, $R_2$ and Y have the meanings previously defined, $R_5$ is an alkyl group of up to 4 carbon atoms, preferably methyl, and A(−) is the anion of an inorganic or organic acid.

The reduction may be effected pursuant to the method indicated above under method B for the reduction of the thioamides; however, as the compounds of the formula V tend to decompose and undergo side-reactions (e.g. hydrolysis, aminolysis), a restriction has to be made. It has proved to be of advantage to continue reacting a compound of the formula V immediately without isolation. The use of a complex metal hydride with reduced reducing power, such as sodium borohydride, is of advantage. Furthermore, it is possible to effect reduction with nascent hydrogen or with hydrogen in the presence of a hydrogenation catalyst, such as Raney nickel. Depending upon the reaction conditions, O-acyl groups may simultaneously be split off in the course of the reduction.

Method D

By Hofmann's degradation of a quaternary ammonium compound of the formula

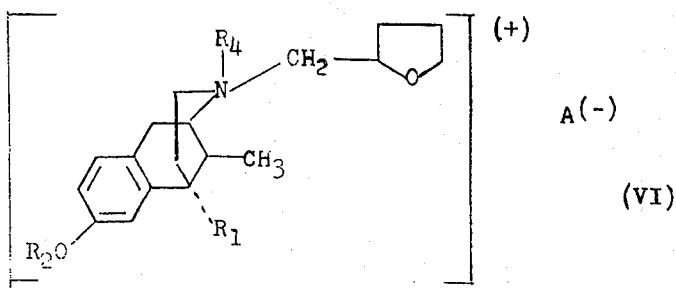

(VI)

wherein $R_1$, $R_2$ and $A(-)$ have the meanings previously defined, and $R_4$ is a group removable by the Hofmann Elimination, such as β-phenylethyl, naphthylethyl or 1,2-diphenylethyl.

The reaction is effected by the action of a base upon the quaternary salt and may be performed in various ways. Under the conditions of the Hofmann Elimination O-acyl groups may be split off, whereby a corresponding compound of the formula I is obtained, wherein $R_2$ is hydrogen.

Method E

By cyclizing a compound of the formula wherein $R_1$ and $R_2$ have the meanings previously defined and Z is halogen, hydroxyl, alkoxy, acyloxy, arylsulfonyloxy or alkylsulfonyloxy.

The cyclization reaction is performed under the conditions of the Friedel-Crafts Reaction with aluminum chloride in carbon disulfide, or with a strong acid, such as phosphoric acid or polyphosphoric acid, preferably at temperatures between 100° and 150°C. Under the cyclization reaction conditions O-acyl or O-alkyl groups may be split off, whereby a compound of the formula I with a free phenolic hydroxyl group ($R_2$ = hydrogen) is obtained.

Method F

By tetrahydrofuran ring closure of a compound of the formula

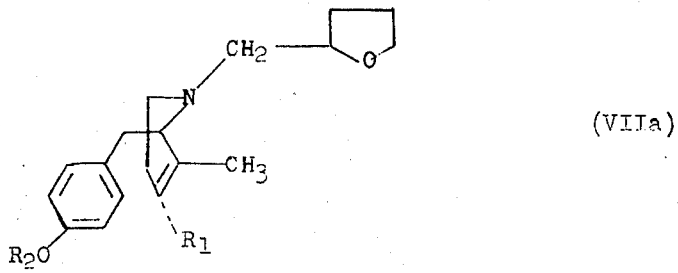

(VIIa)

or

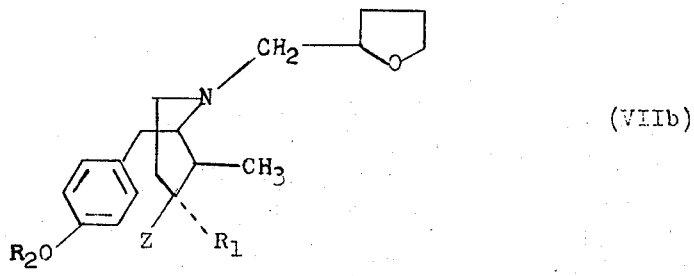

(VIIb)

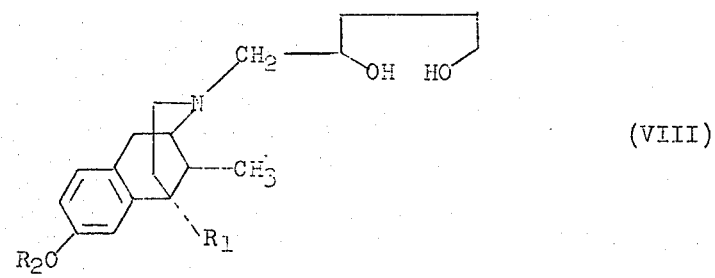

(VIII)

wherein $R_1$ and $R_2$ have the meanings previously defined.

For example, the dehydration leading to cyclization of the tetrahydrofuran ring may be brought about by the action of an acid catalyst upon a compound of the formula VIII. Suitable acid catalysts are, for example, inorganic or organic acids or acid salts, such as sulfuric acid, phosphoric acid, oxalic acid, p-toluenesulfonic acid, sodium bisulfate or anhydrous zinc chloride. The reaction is preferably carried out at elevated temperatures, most advantageously between 100° and 200°C. It is of advantage to remove the water which is split off with the aid of water-binding agents, such as an excess of sulfuric acid or zinc chloride, or by azeotropic distillation. Frequently, it is of advantage to replace one of the two hydroxyl groups intermediately by a more reactive group. Thus, for example, the cyclization may be effected with toluenesulfonic acid chloride in pyridine without isolating the o-toluenesulfonyloxy-derivative of the compound of the formula VIII which is intermediately formed. Depending upon the relative severity of the reaction conditions, O-acyl and O-alkyl groups may simultaneously be split into free phenolic hydroxyl groups, whereby a compound of the formula I, wherein $R_2$ is hydrogen, is obtained.

Method G

A compound of the formula I wherein $R_2$ is hydrogen is obtainable by ester cleavage of a compound of the formula

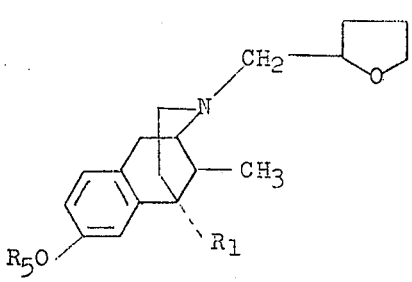

(IX)

wherein $R_1$ has the meanings previously defined and $R_5$ is an acyl group derived from an inorganic or organic acid. Examples of such acyl groups are, above all, lower aliphatic or simple aromatic and heterocyclic acyl groups, in particular acetyl, propionyl, benzoyl and tetrahydro-2-furoyl groups.

The cleavage may be effected by acid or alkaline hydrolysis, which is preferably carried out in aqueous, alcoholic or aqueous-alcoholic solution. The reaction temperature, which is variable within wide limits, lies advantageously between 20° and 100°C.

The O-acyl grouping may also be split reductively. Among the applicable processes, the reduction with a complex hydride is especially suitable. The reductive cleavage is carried out in analogy to the procedure described under Method B for reduction of the carboxylic acid amides. It is of advantage to reduce simultaneously the amide and phenol ester grouping.

Method H

By ether cleavage of a compound of the formula

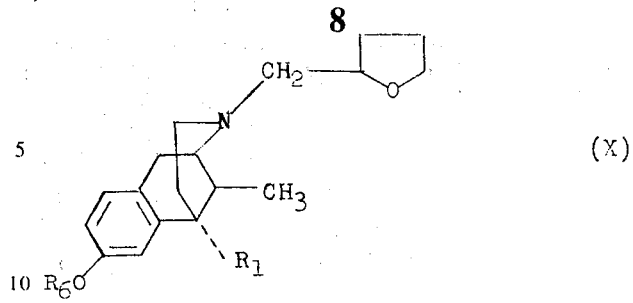

(X)

wherein $R_1$ has the meanings defined above, and $R_6$ is alkyl or aralkyl, whereby a compound of the formula I wherein $R_2$ is hydrogen is obtained.

The ether cleavage of a compound of the formula X must be effected in such a way that the tetrahydrofuran ring remains intact. A suitable method, for example, is the selective cleavage of the phenol ether grouping with caustic soda and caustic potash in a high-boiling-point solvent, such as diethyleneglycol or triethyleneglycol. This reaction is advantageously carried out at temperatures between 150°C and the boiling point of the solvent with an excess of alkali metal hydroxide. Benzyl ethers may also be split by catalytic hydrogenation. Methoxymethyl ethers are very unstable in the presence of acids and can be split even under mild conditions with dilute mineral acids.

Method I

By acylation of a compound of the formula I wherein $R_2$ is hydrogen to form a compound of the formula I wherein $R_2$ is acetyl.

The acetylation is most advantageously effected with acetyl chloride or acetic acid anhydride in an inert solvent, using a calculated amount or a slight excess of the acetylating agent. However, it is also possible to use a greater excess of the acetylating agent, which then serves simultaneously as the solvent medium. It is recommended to add to the reaction mixture an acid-binding agent. Pyridine is especially suitable for this purpose; it can be provided in catalytic amounts, in equimolar amounts or in greater excess so as to serve as a solvent. Another base well suited for this purpose is triethylamine. As reaction temperature the range from 20° to 150°C, preferably 50° to 100°C, has proved to be especially suitable.

Method K

By methylating a compound of the formula I wherein $R_4$ is hydrogen to form a compound of the formula I wherein $R_4$ is methyl.

The alkylation is preferably effected under reaction conditions which allow for a selective O-methylation without quaternization of the nitrogen. For this purpose the use of diazomethane or phenyltrimethyl-ammonium-hydroxide as the alkylation agent is particularly suitable. With diazomethane the alkylation is performed in a suitable inert solvent, such as in diethyl ether or tetrahydrofuran, preferably at room temperature. When using phenyl trimethyl-ammonium-hydroxide, the starting compound is heated with the alkylating agent in a suitable inert solvent, preferably in dimethylformamide.

The reaction products of the formula I obtained by the above-described methods A-K are isolated from the reaction mixtures with the aid of conventional procedures. If required, the crude products obtained may be purified by using special processes, such as column-chromatography, before they are crystallized in form of the free bases or suitable acid addition salts.

Depending upon the reaction conditions and reaction partners, the reaction products thus obtained are either sterically uniform compounds or mixtures of racemic or optically active diastereoisomers.

Diastereoisomers may be separated pursuant to known processes, which make use of their differing chemical and physical properties, for example, by fractional crystallization. Racemic compounds may be separated into the corresponding optical antipodes by conventional methods for racemate separation.

Most of the starting compounds needed for methods A-K above are known. Thus, for example, the norbenzomorphans of the formula II are repeatedly described in the literature.

The optically active tetrahydrofurfuryl halides of the formula III may be produced from the known optically active alcohols [F. C. Hartmann and R. Barker, J. Org. Chem. 29, 873–877 (1964)] by halogenation, for instance with phosphorus pentachloride or phosphorus pentabromide (Org. Synth. 23, 88).

L-(+)-tetrahydrofurfuryl alcohol: $[\alpha]_D^{25} = +15.3°$ ($c = 5$, nitromethane)
b.p. 76°C/ 16 mm Hg D-(−)-tetrahydrofurfuryl alcohol: $[\alpha]_D^{25} = -15.7°$ ($c = 5$, nitromethane)
b.p. 76°C/ 16 mm Hg L-(+)-tetrahydrofurfuryl bromide: $[\alpha]_D^{25} = +3.9°$ (c = 5, nitromethane)
b.p. 66°–67°C/ 16 mm Hg D-(−)-tetrahydrofurfuryl bromide: $[\alpha]_D^{25} = -3.8°$ ($c = 5$, nitromethane)
b.p. 67°C/ 16 mm Hg By reacting the tetrahydrofurfuryl alcohols with sulfonic acid halides, the corresponding sulfonic acid esters can be prepared.

Carboxylic acid amides of the formula IV are obtained by reacting the nor-compounds of the formula II with tetrahydrofuroyl chlorides. From the corresponding carbonamides of the formula IV the corresponding thiocarbonamides may be produced by reaction with phosphorus pentasulfide.

Compounds of the formula V are obtained by reacting compounds of the formula IV with alkylating agents.

Compounds of the formula VI are produced by reacting nor-compounds of the formula II with β-phenylethyl chloride, naphthylethyl chloride or 1,2- diphenylethyl chloride, and subsequently quaternizing the resulting tertiary amines with compounds of the formula III.

The starting compounds of the formulas VIIa and VIIb are accessible by alkylating piperidines of the formulas

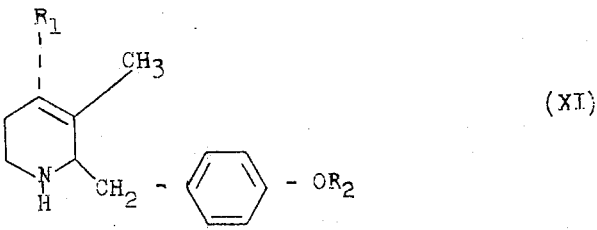

(XI)

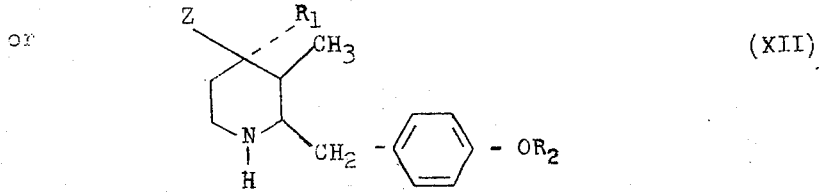

(XII)

wherein $R_1$ through $R_2$ and Z have the meanings previously defined, which are described in the literature.

The starting compounds of the formula VIII are produced by reacting nor-compounds of the formula II with γ-keto-acid esters of the formula

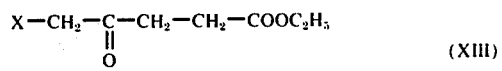

(XIII)

wherein X has the previously defined meanings, and reducing the intermediate compound of the formula

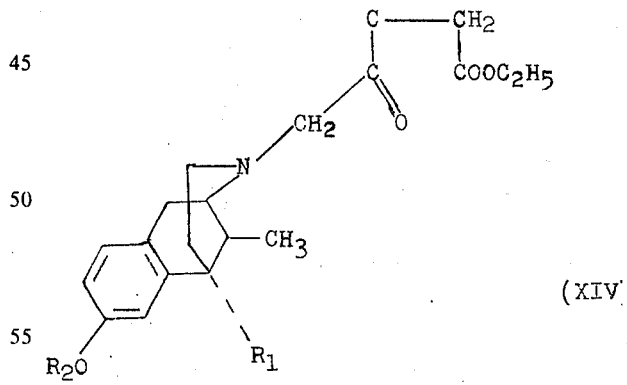

(XIV)

thus obtained with complex hydrides.

The starting compounds of the formulas IX and X are accessible by alkylating corresponding norbenzomorphans with alkylating agents of the formula III.

The compounds of the formula I are organic bases and therefore form acid addition salts with inorganic or organic acids. Examples of non-toxic, pharmacologically acceptable acid addition salts are those formed with hydrochloric acid, hydrobromic acid, hydro-iodic acid, hydrofluoric acid, sulfuric acid, phosphoric acid, nitric acid, acetic acid, propionic acid, butyric acid, valeric acid, pivalic acid, caproic acid, oxalic acid, malonic acid, succinic acid, maleic acid, fumaric acid, lactic acid, tartaric acid, citric acid, malic acid, benzoic acid, p-amino-benzoic acid, p-hydroxy-benzoic acid, phthalic acid, terephthalic acid, cinnamic acid, salicylic acid, ascorbic acid, 8-chlorotheophylline, methanesulfonic acid, benzenesulfonic acid, ethanephosphoric acid, or the like.

The following examples illustrate the present invention and will enable others skilled in the art to understand it more completely. It should be understood, however, that the invention is not limited solely to the particular examples given below.

EXAMPLE 1

(−)-2-(L-Tetrahydrofurfuryl)-[(1R, 5R, 9S)-2′-hydroxy-5,9-dimethyl-6,7-benzomorphan] by method A 6.5 gm (0, 3 mol) of (1R, 5R, 9S)-(−)-2′-hydroxy-5,9-dimethyl-6,7-benzomorphan, 3.8 gm of sodium bicarbonate and 5.46 gm (0.33 mol of L-(+)-tetrahydrofurfuryl bromide were heated at 95°–100°C in 60 ml of dimethylformamide for 14 hours, while stirring. Subsequently, the reaction mixture was evaporated in vacuo, and the residue was shaken with a mixture of 100 ml of chloroform an 100 ml of water. After separation of the chloroform phase in a separating funnel, the aqueous solution was extracted twice with 15 ml of chloroform each. The combined chloroform extracts were washed with 50 ml of water, dried over sodium sulfate and evaporated in vacuo. The crude reaction product thus obtained as the evaporation residue may be crystallized as such or, more preferably, after purification by column-chromatography on aluminum oxide. For column-chromatography, the crude product was dissolved in 75 ml of chloroform, and the solution was introduced into a chromatography column charged with 100 gm of aluminum oxide (activity stage III, neutral) in chloroform. The column was eluted with a mixture of 99 parts of volume of chloroform and 1 part of volume of methanol, and the eluate was collected in fractions of 25 ml. After thin-layer chromatographic examination, the fractions containing the pure substance were combined and evaporated in vacuo. The evaporation residue was dissolved in 35 ml of methanol, and the solution was admixed with 35 ml of water. After standing overnight at 2°C, the crystallizate was collected by suction filtration, washed with aqueous methanol and dried at 80°C. 5.9 gm (65.3% of theory) of the crystalline base, m.p. 171°C, were obtained; its melting point remained unchanged after recrystallization from aqueous methanol. The product had a specific rotation of $[\alpha]_D^{25} = -112°(c = 1,$ methanol).

EXAMPLE 2

(+)-2-(D-Tetrahydrofurfuryl)-[(1S, 5S, 9R)-2′-hydroxy-5,9-dimethyl-6,7-benzomorphan] by method A.

A mixture consisting of 6.5 gm (0.03 mol) of (1S,5S, 9R)-(+)-2′-hydroxy-5,9-dimethyl-6,7-benzomorphan, 3.8 gm (0.015 mol) of sodium bicarbonate, 5.42 gm (0.033 mol) of D-(−)-tetrahydrofurfuryl bromide and 60 ml of dimethylformamide was maintained at a temperature of 95°–100°C for eight hours, while stirring. The heater was then turned off and, while continuing the stirring, the reaction mixture was admixed at a rapid dropwise rate with 150 ml of water, whereby a crystalline precipitate was formed. After standing overnight in a refrigerator, the precipitate was collected by suction filtration, thoroughly washed with several portions of water, and dried at 80°C until the weight remained constant, yielding 6.3 gm (69.5% of theory) of the raw reaction product having a melting point of 166°C. After recrystallization from methanol/water, the product had a melting point of 171°C and a specific rotation of $[\alpha]_D^{25} = +112°$ ($c = 1$, methanol). The product thus obtained, which is named in the heading, was the optical antipode of the compound obtained as the end product in Example 1.

EXAMPLE 3

(−)-2-(D-Tetrahydrofurfuryl)-[(1R, 5R, 9S)-2′-hydroxy-5,9-dimethyl-6,7-benzomorphan] by method A.

A mixture consisting of 13.0 gm (0.06 mol) of (1R, 5R, 9S)-(−)-2′-hydroxy-5,9-dimethyl-6,7-benzomorphan, 7.6 gm of sodium bicarbonate, 10.9 gm (0.066 mol) of D-(−)-tetrahydrofurfuryl bromide and 120 ml of dimethylformamide was maintained at a temperature of 95°–100°C for 14 hours while stirring. Thereafter, the reaction mixture was worked up in analogy to Example 1, the raw product was purified by column chromatography, and the purified product was crystallized from aqueous methanol, yielding 12.1 gm (66.5% of theory) of the desired product named in the heading, which had a melting point of 141°C. After recrystallization from aqueous methanol, it had a melting point of 144°C and a specific rotation $[\alpha]_D^{25} = -102°$ (c = 1, methanol).

EXAMPLE 4

(+)-2-(L-Tetrahydrofurfuryl)-[(1S, 5S, 9R)-2′-hydroxy-5,9-dimethyl-6,7-benzomorphan] by method A.

Using a procedure analogous to that described in Example 2, 6.5 gm (0.03 mol) of 1S, 5S, 9R)-(+)-2′-hydroxy-5,9-dimethyl-6,7-benzomorphan, 3.8 gm (0.015 mol) of sodium bicarbonate and 5.42 gm (0.033 mol) of L-(+)-tetrahydrofurfuryl bromide were reacted, and the reaction product was isolated. 5.8 gm (64.0% of theory) of the compound named in the heading, which had a melting point of 143°C, were obtained. After recrystallization from methanol/water, the product had a melting point of 144°C and a specific rotation $[\alpha]_D^{25} = +102°C$ ($c = 1$, methanol). The product thus obtained was the optical antipode of the end product obtained in Example 3.

EXAMPLE 5

(−)-2-(L-tetrahydrofurfuryl)-[(1R,5R,9S)-2′-hydroxy-5,9-dimethyl-6,7-benzomorphan] and (−)-2-(D-tetrahydrofurfuryl)-1[(1R,5R,9S)-2′-hydroxy-5,9dimethyl-6,7-benzomorphan] by method A A mixture consisting of 6.5 gm (0.03 mol) of (1R, 5R,9S)-(−)-2′-hydroxy-5,9-dimethyl-6,7-benzomorphan, 3.8 gm of sodium bicarbonate, 5.46 gm (0.033 mol) of DL-tetrahydrofurfuryl bromide and 60 ml of dimethylformamide was heated at 100°C for 8 hours, while stirring. Thereafter, the heating bath was removed, and the reaction mixture was admixed dropwise with 300 of water, whereupon the reaction product separated out in crystalline form. After standing in the refrigerator overnight, the crystalline substance was collected by suction filtration, washed three times with water, and dried at 80°C, yielding 6.35 gm of a mixture of the two diastereoisomeric compounds named in the heading.

An additional amount of the diastereoisomeric mixture was obtained from the filtrate. For this purpose the filtrate was evaporated in vacuo, the residue was shaken with a mixture consisting of 50 ml of chloroform and 50 ml of water, and the two phases were separated in a separating funnel. The aqueous phase was again extracted with 25 ml of chloroform, and the chloroform solutions were combined, washed with water, dried with sodium sulfate, and evaporated in vacuo. The evaporation residue (2.0 gm) was purified by filtering it through an aluminum oxide column. For this purpose the evaporation residue was dissolved in 20 ml of chloroform, and the solution was allowed to pass slowly through a column charged with 25 gm of aluminum oxide (activity stage III, neutral). The column was then washed with 40 ml of chloroform, and the chloroform solutions were combined and evaporated in vacuo. The resulting evaporation residue (0.6 gm), which consisted of a mixture of the two diastereoisomeric compounds named in the heading, was combined with the previously obtained crystalline diastereoisomeric mixture, making a total yield of 6.95 gm (77% of theory). After recrystallization from a boiling mixture of 160 ml of methanol and 80 ml of water, 5.5 gm of crystallizate and then 0.5 gm of additional crystallizate, each having a melting point of 164°165°C, were obtained.

The presence of the two diastereoisomers in the crystallizate was proven by thin-layer chromatography, and they can also be separated in this manner. Thus, chromatography on silicagel plates, using toluene/methanol (7:3) as a flow agent, produced two substance spots at $R_f$-values 0.6 and 0.7 (iodine chamber). The same chromatographic picture is produced by a mixture of the individual end products obtained in Examples 1 and 3, respectively, where the product of Example 1 had an $R_f$-value of 0.7, and the product of Example 3 had an $R_f$-value of 0.6.

EXAMPLE 6

2-Tetrahydrofurfuryl-2'-hydroxy-5,9β-dimethyl-6,7-benzomorphan (mixture of racemic diastereoisomers I and II by method A.

Using a procedure analogous to that described in Example 1, 6.5 gm (0.03 mol) of (+)-2'-hydroxy-5,9β-dimethyl-6,7-benzomorphan were reacted with 5.46 gm (0.033 mol) of D, L-tetrahydrofurfuryl bromide in the presence of 3.8 gm of sodium bicarbonate and 0.4 gm of potassium iodide, and the reaction product was isolated and purified by chromatography on aluminum oxide. The purified compound was crystallized from 170 ml of aqueous 70% methanol, the mixture was allowed to stand overnight in the refrigerator, and the crystallizate was then collected by suction filtration, washed with a little aqueous methanol and dried at 80°C, yielding 7.0 gm (77.5% of theory) of a substance having a melting point of 144°–146°C.

The product thus obtained was a mixture of the two racemic diastereoisomers I and II, which was confirmed as follows: Thin-layer chromatography on silicagel plates with toluene/methanol (7:3) produced two substance spots at $R_f$-values 0.6 and 0.7 (iodine chamber). The racemic diastereoisomer I having the $R_f$-value was composed of the two optical antipodes obtained individually in Examples 1 and 2, respectively. The racemic diastereoisomers II having the $R_f$-value 0.6 was composed of the two optical antipodes obtained individually in Examples 3 and 4, respectively.

EXAMPLE 7

2-(L-Tetrahydrofurfuryl)-[(1R,5R,9S)-2'-hydroxy-5-phenyl-9-methyl-6,7-benzomorphan] by method A A mixture consisting of 3.16 gm (10 millimols) of (1R,5R,9S)-(−)-2'-hydroxy-5-phenyl-9-methyl-6,7-benzomorphan hydrochloride, 1.82 gm (11 millimols) of L-(+)-tetrahydrofurfuryl bromide, 2.52 gm (30 millimols) of sodium bicarbonate and 50 ml of dimethyl formamide was stirred at 100°C until the reaction had gone to completion (4 to 6 hours). Thereafter, the reaction mixture was evaporated in vacuo at 70°C, and the residue was taken up in a mixture consisting of 100 ml of methylene chloride, 20 ml of n-butanol and 50 ml of water. The organic phase was separated, washed five times with 50 ml of water each, dried over sodium sulfate and evaporated. The residue was recrystallized from a little ethanol, yielding 2.6 gm (71.6% of theory) of the compound named in the heading, which had a melting point of 192°–198°C.

EXAMPLE 8

Using a procedure analogous to that described in Example 7, 69.8% of theory of 2-(D-tetrahydrofurfuryl)-[(1R, 5R,9S)-2'-hydroxy-5-phenyl-9-methyl-6,7-benzomorphan], m.p. 145°–146°C (from ethanol), was obtained from (1R,5R,9S)-(−)-2'-hydroxy-5-phenyl-9-methyl-6,7-benzomorphan hydrochloride and D-(−)-tetrahydrofurfuryl bromide.

EXAMPLE 9

(−)-2-(L-Tetrahydrofurfuryl)-[(1R,5R,9S)-2'-acetoxy-5,9-dimethyl-6,7-benzomorphan] by method I 3.01 gm (0.01 mol) of (−)-2-(L-tetrahydrofurfuryl)-[(1R,5R,9S)-2'-hydroxy-5,9-dimethyl-6,7-benzomorphan] were heated on a boiling water bath with 25 ml of acetic acid anhydride for 30 minutes. Subsequently, the reaction solution was evaporated in vacuo, and the residue was stirred for several minutes with a mixture consisting of 100 gm of ice and 100 ml of water. After addition of 100 ml of ether, the mixture was made just alkaline with 2 N ammonia, while stirring was continued. The ether phase was separated, and the aqueous phase was once more extracted with 50 ml of ether. The combined ethereal extracts were washed three times with each 50 ml of water, dried with sodium sulfate and evaporated in vacuo, leaving the compound named in the heading in the form of a yellowish syrup. The product was thin-layer chromatographically pure and an $R_f$-value of 0.7, compared to the $R_f$-value of 0.5 of the starting compound (silicagel; chloroform/methanol/concentrated ammonia = 80:20:1).

EXAMPLE 10

(−)-2-(D-Tetrahydrofurfuryl)-[(1R,5R,9S)-2'-methoxy-5,9-dimethyl-6,7-benzomorphan by method K.

1.6 gm (0.052 mol) of (−)-2-(D-tetrahydrofurfuryl)-[(1R,5R,9S)-2'-hydroxy-5,9-dimethyl-6,7-benzomorphan] were admixed first with 4 ml of methanol and then with 0.99 gm (0.0057 mol) of phenyl trimethylammonium chloride. A clean solution was formed, to which 0.28 of sodium methylate and 10 ml of absolute dimethyl formamide were added. The solvent mixture was then distilled off, the residue was dissolved with 5 ml of fresh absolute dimethylformamide, and the solution was refluxed for 2 hours. After cooling it was shaken in a separating funnel with a mixture of 50 ml of 2 N NaOH and 50 ml of chloroform. After separation of the phases, the aqueous phase was extracted once more with 25 ml of chloroform, the combined chloroform phases were washed with water, dried with sodium sulfate and evaporated in vacuo. The residue was purified by chromatography on aluminum oxide analogous to Example 1. The eluate fractions containing the pure product were combined and evaporated in vacuo. The compound named in the heading was obtained as a yellowish evaporation residue, which had an $R_f$-value of 0.65 in the thin-layer chromatogram (silicagel plates; chloroform/methanol/concentrated ammonia = 90:10:0.5). The starting compound has an $R_f$-value of 0.05 under the same conditions.

EXAMPLE 11

(−)-2-(L-Tetrahydrofurfuryl)-[(1R,5R,9S)-2'-hydroxy-5,9-dimethyl-6,7-benzomorphan hydrochloride 15.3 gm of (−)-2-(L-tetrahydrofurfuryl)-[(1R,5R,9S)-2'-hydroxy-5,9-dimethyl-6,7-benzomorphan] were dissolved in a mixture of 80 ml of ethanol and 40 ml of 2N hydrochloric acid, and 200 ml of absolute ether were added to the solution. The mixture was allowed to stand in the refrigerator overnight, whereupon the crystalline precipitate which had formed was suction-filtered off, washed first with a mixture (1:1) of ethanol and then only with ether, then air-dried and finally dried at 80°C. 15.7 gm (81.5% of theory) of the hydrochloride were obtained, which had a melting point of 257°C; it remained unchanged after recrystallization from ethanol/ether.

EXAMPLE 12

Using a procedure analogous to that described in Example 11, 8.0 gm (79.1% of theory) of (+)-2-(D-tetrahydrofurfuryl)-[(1S,5S,9R)-2'-hydroxy-5,9-dimethyl-6,7-benzomorphan]hydrochloride, m.p. 257°C, were obtained from 8.2 gm of the free base. The melting point did not change after recrystallization.

EXAMPLE 13

Using a procedure analogous to that described in Example 11, 14.8 gm (79.6% of theory) of (−)-2-(D-tetrahydrofurfuryl)-[(1R,5R,9S)-2'-hydroxy-5,9-dimethyl-6,7-benzomorphan]hydrochloride, m.p. 290°–291°, were obtained from 14.7 gm of the free base. The melting point did not change after recrystallization.

EXAMPLE 14

Using a procedure analogous to that described in Example 11, 5.4 gm (79.5% of theory) of (+)-2-(L-tetrahydrofurfuryl)-[(1S,5S,9R)-2'-hydroxy-5,9-dimethyl-6,7-benzomorphan] hydrochloride, m.p. 290°–291°C, were obtained from 5.0 gm of the free base. The melting point did not change after recrystallization.

The compounds of the present invention, that is, those embraced by formula I above and their non-toxic, pharmacologically acceptable acid addition salts, have useful pharmocodynamic properties. More particularly, the compounds of this invention exhibit strong analgesic activities in warm-blooded animals, such as mice. In various pharmacological tests on mice, such as the Haffner test, the hot-plate test and the writhing test, the analgesic activity of the compounds of the present invention was found to be ten to thirty times greater than that of morphine. However, they differ from morphine by the absence of the typical morphine side-effects in mice, such as Straub's tail, running in circles and the like, which, according to current literature teachings, is strongly indicative of the absence of addictive properties [see, for example, I. Schemano et al, A Rapid Screening Test for Potential Addiction Liability of New Analgesic Agents, Toxicol. Appl. Pharmacol. 6, 334–339 (1964)]. In addition, the compounds of this invention exhibit a significantly greater therapeutic ratio than morphine and produce no morphine-like effects in morphine-addicted rats.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from about 0.0083 to 1.67 mgm/kg body weight, preferably 0.016 to 0.33 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 15

Tablets

The tablet composition is compounded from the following ingredients:

| | |
|---|---|
| (−)-2-(D-Tetrahydrofurfuryl)-[(1R,5R,9S)-2'-hydroxy-5,9-dimethyl-6,7-benzomorphan] methanesulfonate | 20.0 parts |
| Lactose | 120.0 parts |
| Corn Starch | 50.0 parts |
| Colloidal silicic acid | 2.0 parts |
| Soluble Starch | 5.0 parts |
| Magnesium stearate | 3.0 parts |
| Total | 200.0 parts |

Preparation:

The benzomorphan compound is intimately admixed with the lactose and the corn starch, the mixture is moistened with an aqueous 10% solution of the soluble starch, the moist mass is forced through a 1mm-mesh screen, the resulting granulate is dried at 40°C, the dry granulate is admixed with the colloidal silicic acid, and the composition is compressed into 200 mgm-tablets in a conventional tablet making machine. Each tablet contains 20 mgm of the benzomorphan and is an oral dosage unit composition with very effective analgesic action.

EXAMPLE 16

Coated pills

The pill core composition is compounded from the following ingredients:

| | |
|---|---|
| (−)-2-(D-Tetrahydrofurfuryl)-[(1R,5R,9S) -2′-hydroxy-5,9-dimethyl-6,7-benzomorphan] methanesulfonate | 15.0 parts |
| Lactose | 100.0 parts |
| Corn starch | 95.0 parts |
| Colloidal silicic acid | 2.0 parts |
| Soluble starch | 5.0 parts |
| Magnesium stearate | 3.0 parts |
| Total | 220.0 parts |

Preparation:

The ingredients are compounded in the same manner as in Example 26, and the composition is compressed into 220 mgm-pill cores which are subsequently coated with a thin shell consisting essentially of a mixture of sugar, talcum and gum arabic and finally polished with beeswax. Each coated pill contains 15 mgm of the benzomorphan compound and is an oral dosage unit composition with very effective analgesic action.

EXAMPLE 17

Suppositories

The suppository composition is compounded from the following ingredients:

| | |
|---|---|
| (−)-2-(L-Tetrahydrofurfuryl)-[(1R,5R,9S) -2′-hydroxy-5,9-dimethyl-6,7-benzomorphan] | 10.0 parts |
| Lactose | 150.0 parts |
| Suppository base (e.g. cocoa butter) | 1540.0 parts |
| Total | 1700.0 parts |

Preparation:

The benzomorphan compound is intimately admixed with the lactose, and the mixture is blended with the aid of an immersion, homogenizer into the suppository base which had previously been melted and cooled to about 40°C. 1,700 mgm-portions of the composition are poured into cooled suppository molds and allowed to harden therein. Each suppository contains 10 mgm of the benzomorphan compound and is a rectal dosage unit composition with very effective analgesic action.

EXAMPLE 18

Hypodermic solution

The solution is compounded from the following ingredients:

| | |
|---|---|
| (−)-2-(L-Tetrahydrofurfuryl)-[1R,5R,9S) -2′-hydroxy-5,9-dimethyl-6,7-benzomorphan] | 1.0 parts |
| Sodium chloride | 10.0 parts |
| Double-distilled water q.s.ad | 1000.0 parts by vol. |

Preparation:

The benzomorphan compound and the sodium chloride are dissolved in the double-distilled water, the solution is filtered until free from suspended particles, and the filtrate is filled under aseptic conditions into 5 cc-ampules which are subsequently sterilized and sealed. Each ampule contains 1.0 mgm of the benzomorphan compound, and its contents are an injectable dosage unit composition with very effective analgesic action.

EXAMPLE 19

Drop solution

The solution is compounded from the following ingredients:

| | |
|---|---|
| (±)-2-Tetrahydrofurfuryl-2′-hydroxy- 5,9β-dimethyl-6,7-benzomorphan (racemic diastereoisomer I) | 0.70 parts |
| Methyl p-hydroxy-benzoate | 0.07 parts |
| Propyl p-hydroxy-benzoate | 0.03 parts |
| De-mineralized water q.s.ad | 100.00 parts by vol. |

Preparation:

The benzomorphan compound and the p-hydroxybenzoates are dissolved in the de-mineralized water, the solution is filtered, and the filtrate is filled into 100 cc-bottles. 10 ml of the solution contain 70 mgm of the benzomorphan compound and are an oral dosage unit composition with very effective analgesic action.

Analogous results are obtained when any one of the other compounds embraced by formula I or a nontoxic, pharmacologically acceptable acid addition salt thereof, is substituted for the particular active ingredient in Examples 15 through 19. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

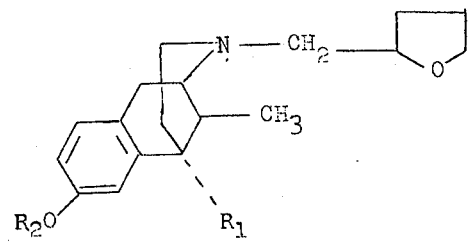

wherein R₁ is methyl or phenyl, and $R_2$ is hydrogen, methyl or acetyl,
or a non-toxic, pharmacologically acceptable acid addition salt thereof.

2. A racemate, racemic mixture of optically active form of a compound of claim 1.

3. A compound of claim 1, which is one of the formula

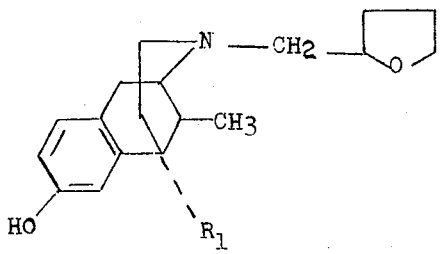

wherein $R_1$ is methyl or phenyl,
or a non-toxic, pharmacologically acceptable acid addition salt thereof.

4. A compound of claim 1, which is (−)-2-(L-tetrahydrofuryl)-[(1R,5R,9S)-2'-hydroxy-5,9-dimethyl-6,7-benzomorphan] or a non-toxic, pharmacologically acceptable acid addition salt thereof.

5. A compound of claim 1, which is (±)-2-tetrahydrofuryl-2'-hydroxy-5,9β-dimethyl-6,7-benzomorphan (racemic diastereoisomer I) or a non-toxic, pharmacologically acceptable acid addition salt thereof.

6. A compound of claim 1, which is (±)-2-tetrahydrofuryl-2'-hydroxy-5,9β-dimethyl-6,7-benzomorphan (racemic diastereoisomer II) or a non-toxic, pharmacologically acceptable acid addition salt thereof.

7. A compound of claim 1, which is (−)-2-(D-tetrahydrofuryl)-[(1R,5R,9S)-2'-hydroxy-5,9-dimethyl-6,7-benzomorphan] or a non-toxic, pharmacologically acceptable acid addition salt thereof.

8. A compound of claim 1, which is 2-(L-tetrahydrofuryl)-[(1R,5R,9S)-2'-hydroxy-5-phenyl-9-methyl-6,7-benzomorphan] or a non-toxic, pharmacologically acceptable acid addition salt thereof.

9. A compound of claim 1, which is 2-D-tetrahydrofuryl)-[(1R,5R,9S)-2'-hydroxy-5-phenyl-9-methyl-6,7-benzomorphan] or a non-toxic, pharmacologically acceptable acid addition salt thereof.

10. An analgesic pharmaceutical dosage unit composition consisting essentially of an inert pharmaceutical carrier and an effective analgesic amount of a compound of claim 1.

11. The method of alleviating pain in a warmblooded animal, which comprises perorally, parenterally or rectally administering to said animal an effective analgesic amount of a compound of claim 1.

* * * * *

PO-1050
(5/69)

UNITED STATES PATENT OFFICE
CERTIFICATE OF CORRECTION

Patent No. 3,982,005      Dated September 21, 1976

Inventor(s) HERBERT MERZ, ADOLF LANGBEIN, GERHARD WALTHER and KLAUS STOCKHAUS

It is certified that error appears in the above-identified patent and that said Letters Patent are hereby corrected as shown below:

In Col. 11, Line 10 and 11      "salicyclic" should read -- salicylic --

In Col. 13, Line 56      "(+)-2'" should read -- ($\pm$)-2' --

Signed and Sealed this

Thirtieth Day of November 1976

[SEAL]

Attest:

RUTH C. MASON
*Attesting Officer*

C. MARSHALL DANN
*Commissioner of Patents and Trademarks*